US012778691B2

(12) United States Patent
Payyavula et al.

(10) Patent No.: US 12,778,691 B2
(45) Date of Patent: Nov. 3, 2026

(54) METHODS AND SYSTEMS FOR COORDINATING CONTENT PRESENTATION FOR COMPUTER-ASSISTED SYSTEMS

(71) Applicant: Intuitive Surgical Operations, Inc., Sunnyvale, CA (US)

(72) Inventors: Govinda Payyavula, Sunnyvale, CA (US); Ryan W. Shaw, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 18/720,756

(22) PCT Filed: Dec. 15, 2022

(86) PCT No.: PCT/US2022/052926
§ 371 (c)(1),
(2) Date: Jun. 17, 2024

(87) PCT Pub. No.: WO2023/114348
PCT Pub. Date: Jun. 22, 2023

(65) Prior Publication Data

US 2025/0057607 A1 Feb. 20, 2025

Related U.S. Application Data

(60) Provisional application No. 63/291,154, filed on Dec. 17, 2021.

(51) Int. Cl.
*A61B 34/30* (2016.01)
*A61B 90/00* (2016.01)
(Continued)

(52) U.S. Cl.
CPC ............ *A61B 34/30* (2016.02); *A61B 90/361* (2016.02); *G16H 40/63* (2018.01); *G16H 50/20* (2018.01); *A61B 2090/367* (2016.02)

(58) Field of Classification Search
None
See application file for complete search history.

(56) References Cited

U.S. PATENT DOCUMENTS

| | | | | |
|---|---|---|---|---|
| 11,007,031 | B2 * | 5/2021 | Fuerst | A61B 90/36 |
| 2006/0109237 | A1 * | 5/2006 | Morita | G16H 40/63 345/156 |

(Continued)

FOREIGN PATENT DOCUMENTS

| | | | |
|---|---|---|---|
| WO | WO-2019232552 A1 * | 12/2019 | G16H 20/40 |

OTHER PUBLICATIONS

International Search Report and Written Opinion for Application No. PCT/US2022/052926, mailed Apr. 6, 2023, 15 pages.

(Continued)

*Primary Examiner* — Ryan Rink
(74) *Attorney, Agent, or Firm* — Osha Bergman Watanabe & Burton LLP

(57) ABSTRACT

A coordination system for coordinating content presentation associated with a session involves using a computer-assisted medical system, the coordination system including a session awareness engine and a content selection engine. The session awareness engine being configured to obtain data from the computer-assisted medical system, the data indicative of an operational state of the computer-assisted medical system and determine a context of the session based on the data. The content selection engine being configured to select a content for presentation to a user of the computer-assisted medical system from a variety of contents by applying a content
(Continued)

selection logic to the context of the session and facilitate presentation of the content to the user.

22 Claims, 8 Drawing Sheets

(51) Int. Cl.

| | |
|---|---|
| ***G16H 40/63*** | (2018.01) |
| ***G16H 50/20*** | (2018.01) |

(56) References Cited

U.S. PATENT DOCUMENTS

| | | | | |
|---|---|---|---|---|
| 2018/0177564 | A1* | 6/2018 | Boutoussov | A61C 1/0015 |
| 2018/0247128 | A1* | 8/2018 | Alvi | G16H 30/20 |
| 2019/0125454 | A1 | 5/2019 | Stokes et al. | |
| 2019/0286844 | A1* | 9/2019 | Gross | G06Q 50/22 |
| 2020/0054412 | A1* | 2/2020 | Fuerst | A61B 90/361 |
| 2021/0134442 | A1* | 5/2021 | Ahn | G16H 30/40 |
| 2021/0205027 | A1* | 7/2021 | Leist | G16H 40/67 |
| 2024/0055127 | A1* | 2/2024 | McNair | G16H 50/30 |

OTHER PUBLICATIONS

Qian L., et al., "A Review of Augmented Reality in Robotic-Assisted Surgery," IEEE Transactions on Medical Robotics and Bionics, Nov. 2019, vol. 2 (1), pp. 1-16.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

METHODS AND SYSTEMS FOR COORDINATING CONTENT PRESENTATION FOR COMPUTER-ASSISTED SYSTEMS

CROSS-REFERENCE TO RELATED APPLICATIONS

This patent application is a U.S. national phase application of International Application No. PCT/US2022/052926, filed on Dec. 15, 2022. International Application No. PCT/US2022/052926 claims the benefit of priority under 35 U.S.C. § 119 (e) to U.S. Provisional Patent Application Ser. No. 63/291,154, filed on Dec. 17, 2021. All mentioned U.S. patent applications, U.S. provisional patent applications, and international applications are incorporated by reference herein in their entirety.

BACKGROUND

Overview

Remote presentation and remote interaction have become more commonplace as persons interact with each other across distances short and long. For example, persons may interact with each other across the room, across cities, across countries, or across oceans and continents. Techniques that help select and present content, e.g., visual and/or audio content, that is appropriate given a current context, can enhance the interaction, locally and remotely, by improving understanding, efficiency and effectiveness of communication, and the like.

Remote presentation and remote interaction can involve robotic systems used to perform tasks at worksites. For example, a robotic system may include robotic manipulators to manipulate instruments for performing the task. Example robotic systems include industrial and recreational robotic systems. Example robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location.

The operation of a robotic system with this level of complexity may be non-trivial. In addition, the procedures that are performed with the robotic systems may also be complex and may require careful planning, in particular when using the robotic system to operate on a patient. Adequate user support may, thus, depend on or may be facilitated by availability of relevant information when needed.

SUMMARY

In general, in one aspect, one or more embodiments relate to a coordination system for coordinating content presentation associated with a session involving use of a computer-assisted medical system. The coordination system comprising: a session awareness engine configured to: obtain data from the computer-assisted medical system, the data indicative of an operational state of the computer-assisted medical system; and determine a context of the session based on the data; and a content selection engine configured to: select a content for presentation to a user of the computer-assisted medical system from a plurality of contents by applying a content selection logic to the context of the session; and facilitate presentation of the content to the user.

In general, in one aspect, one or more embodiments relate to a method for coordinating content presentation associated with a session involving use of a computer-assisted medical system. The method comprising obtaining data from the computer-assisted medical system, the data indicative of an operational state of the computer-assisted medical system; determining a context of the session based on the data; selecting a content for presentation to a user of the computer-assisted medical system from a plurality of contents by applying a content selection logic to the context of the session; and facilitating presentation of the content to the user.

In general, in one aspect, one or more embodiments relate to a non-transitory computer readable medium comprising computer readable program code for coordinating content presentation associated with a session involving use of a computer-assisted medical system. The computer readable program code comprising instructions configured to obtain data from the computer-assisted medical system, the data indicative of an operational state of the computer-assisted medical system; determine a context of the session based on the data; select a content for presentation to a user of the computer-assisted medical system from a variety of contents by applying a content selection logic to the context of the session; and facilitate presentation of the content to the user.

Other aspects will be apparent from the following description and the appended claims.

DETAILED DESCRIPTION

Figure 1A:
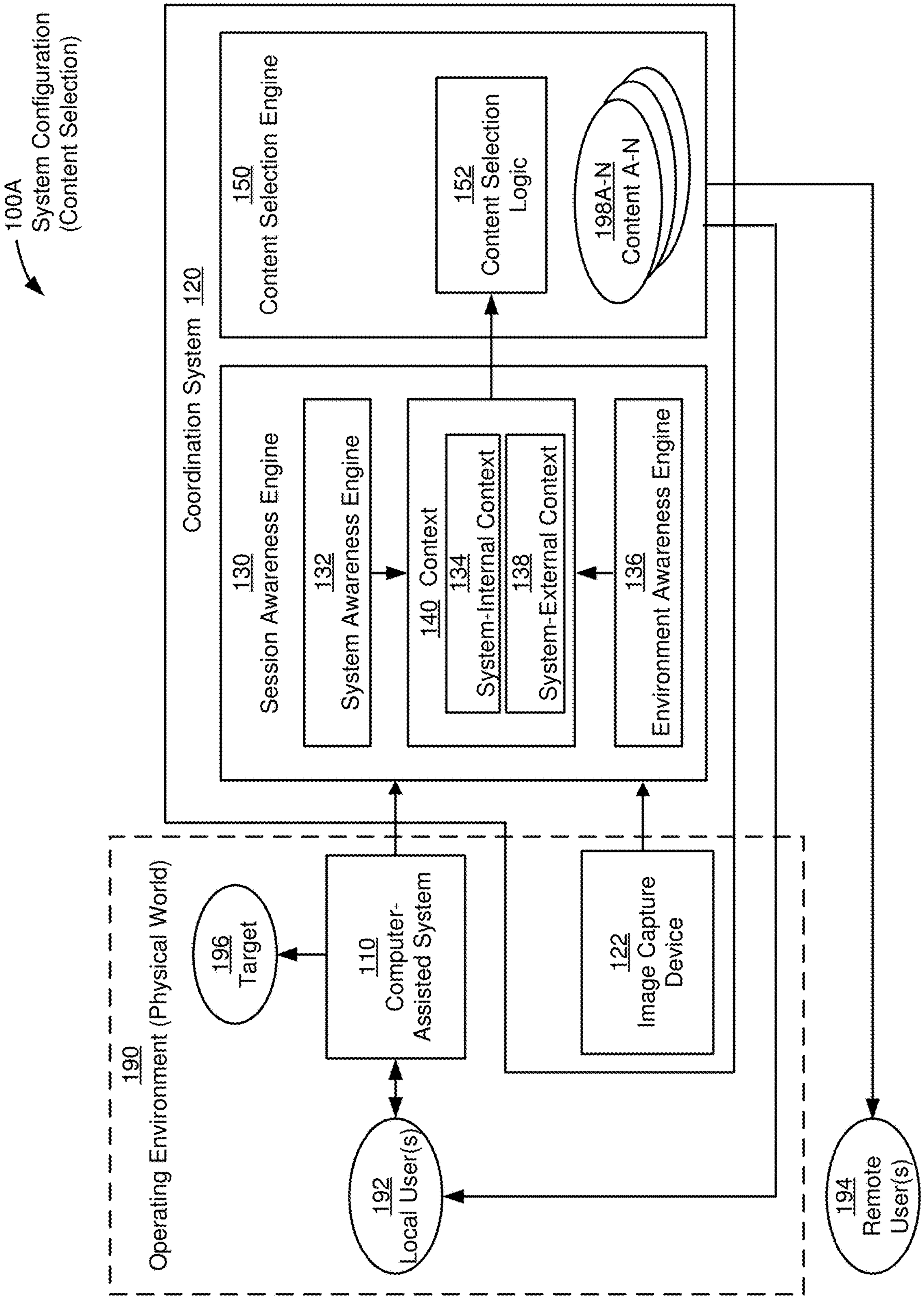
FIG. 1A shows a block diagram of a system configuration, in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosed technique may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms “before”, “after”, “single”, and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or instruments, or medical procedures and medical instruments, the techniques disclosed apply to medical and non-medical procedures, and to medical and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy) and performing procedures on human or animal cadavers. Further, these techniques can also be used for medical treatment or diagnosis procedures that do, or do not, include surgical aspects.

Robotic systems in accordance with one or more embodiments may be complex. For example, a robotic system may include multiple links coupled together by multiple joints. Some or all of these joints may be user-controllable via control algorithms enabling coordinated joint movement. Further, some of these joints may be capable of operating in different modes, depending on task requirements. The robotic system may also be equipped with an instrument. The instrument may have multiple degrees of freedom and different types of instruments may be interchangeably used. The operation of a robotic system with this level of complexity may be non-trivial. In addition, the procedures that are performed with the robotic systems may also be complex and may require careful planning, in particular when using the robotic system to operate on a patient. Providing adequate user support may, thus, be beneficial or even essential.

In one or more embodiments, a computer-assisted robotic system is a component of a computer-assisted system used during a session such as a surgery, a support session, a teaching session, or any other type of activity involving the computer-assisted robotic system. In the computer-assisted system, additional components may provide support to users of the computer-assisted robotic system during the session. User support may be provided in the form of visual and/or audio content, for example, using telepresence as further described below. During a telepresence event, one or more remote users may communicate with one or more local users of the computer-assisted robotic system. Depending on the current context, different content may be provided to the remote and or local user to support their use of the computer-assisted robotic system. As discussed in detail below, many different types of content may exist, and some content may be more useful than other content, based on the current context. Context may include any variable that may affect the selection of content to be provided. Consider, for example, a session involving a computer-assisted robotic system that is used for a medical procedure on a patient in an operating room. Different local and remote users may be involved in the procedure. For example, there may be one or more bedside assistants, a surgeon, a circulating nurse, etc. In other sessions, the use of telepresence may be for different reasons. For example, telepresence may be used for remote proctoring, remote mentoring, remote case observation, remote technical support, etc. Also, the medical procedure may progress through different phases, the computer-assisted robotic system itself may operate in different states, including error states, etc. All of these elements may contribute to the current context. Depending on the current context, it may be advantageous to provide different types of content and/or different views of the content to the remote and/or local user(s). For example, for one context, the most relevant content to be provided may include an endoscope view. For another context, the most relevant content to be provided may include a bedside view. Having the most relevant content automatically presented to the remote and/or local user may reduce delays, cognitive load, and missed information by eliminating the need for the remote and/or local user to select from a multitude of available contents, and having to manipulate the content (e.g., by zooming, panning, 3D-orienting), etc.

In general, embodiments of the disclosure may coordinate content presentation to users of a computer-assisted system that is or includes a computer-assisted robotic and/or computer-assisted medical system. The coordination of content presentation may involve, for example, an identification of content that is appropriate given a current context and providing the identified content to one or more users in a format considered beneficial.

Context may be gathered from the computer-assisted robotic or computer-assisted medical system itself (system-internal context) and/or be gathered from observing the operating environment in which the system operates and/or any other relevant space or resource (system-external context). Context may be used in order to select content for presentation to the user(s), from a multitude of contents. The content may be selected in order to address a need or desire for information of the user(s). Among the multitudes of contents, some content may address this need or desire in a better manner than some other content. Based on the context, in one or more embodiments, the content that is considered suitable to address this need or desire is selected for presentation to the user(s).

In one or more embodiments, the computer-assisted robotic or computer-assisted medical system includes numerous components. At any time, the computer-assisted robotic or computer-assisted medical system may have a current operational state. The operational state may be described using variables such as the current kinematic configuration, error conditions, etc. Many variables may be used to characterize an operational state. At least some of the variables characterizing the operational state may be captured to establish a system-internal context. For example, the system-internal context may include a status of a robot manipulator of the system (e.g., including a kinematic configuration), or the status of instruments that are or may potentially be attached instruments, may be detected using one or more sensors. Further examples of variables that may be included in the system-internal context may be variables that indicate whether a portion of the system has been draped, whether (in a medical example) a cannula for guiding a medical instrument is connected to the computer-assisted medical system, whether and which errors or faults have been detected in the operation of the system, etc. Any obtainable variable associated with the operational state may be included in the system-internal context. Examples of system-external context include information about the operating environment external to the computer-assisted robotic or medical system, which may be obtained by a computerized vision system or in other ways. For example, image data about the workspace of the computer-assisted robotic or medical system may be used to identify the current stage of a procedure being performed using the computer-assisted medical or robotic system. Similarly, the types of users being present in the operating environment, their locations, etc. may be considered system-external context. In combination, the system-internal context and the system-external context form the context.

A detailed description of systems and methods incorporating these, and other features is subsequently provided. Embodiments of the disclosure may be used for various purposes including, but not limited to, facilitating technical support, remote proctoring, teaching, etc., in various fields such as manufacturing, recreation, servicing and maintenance, computer-aided medical procedures including robotic surgery, and field services in general. For example, embodiments of the disclosure may provide support for setting up, cleaning, maintaining, servicing, operation a computer-assisted medical system, etc. In addition or alternatively, embodiments of the disclosure may be used for remote proctoring, where a more experienced user guides a less experienced user on operating a computer-assisted medical system, such as on aspects of performing a surgical procedure.

Figure 1B:
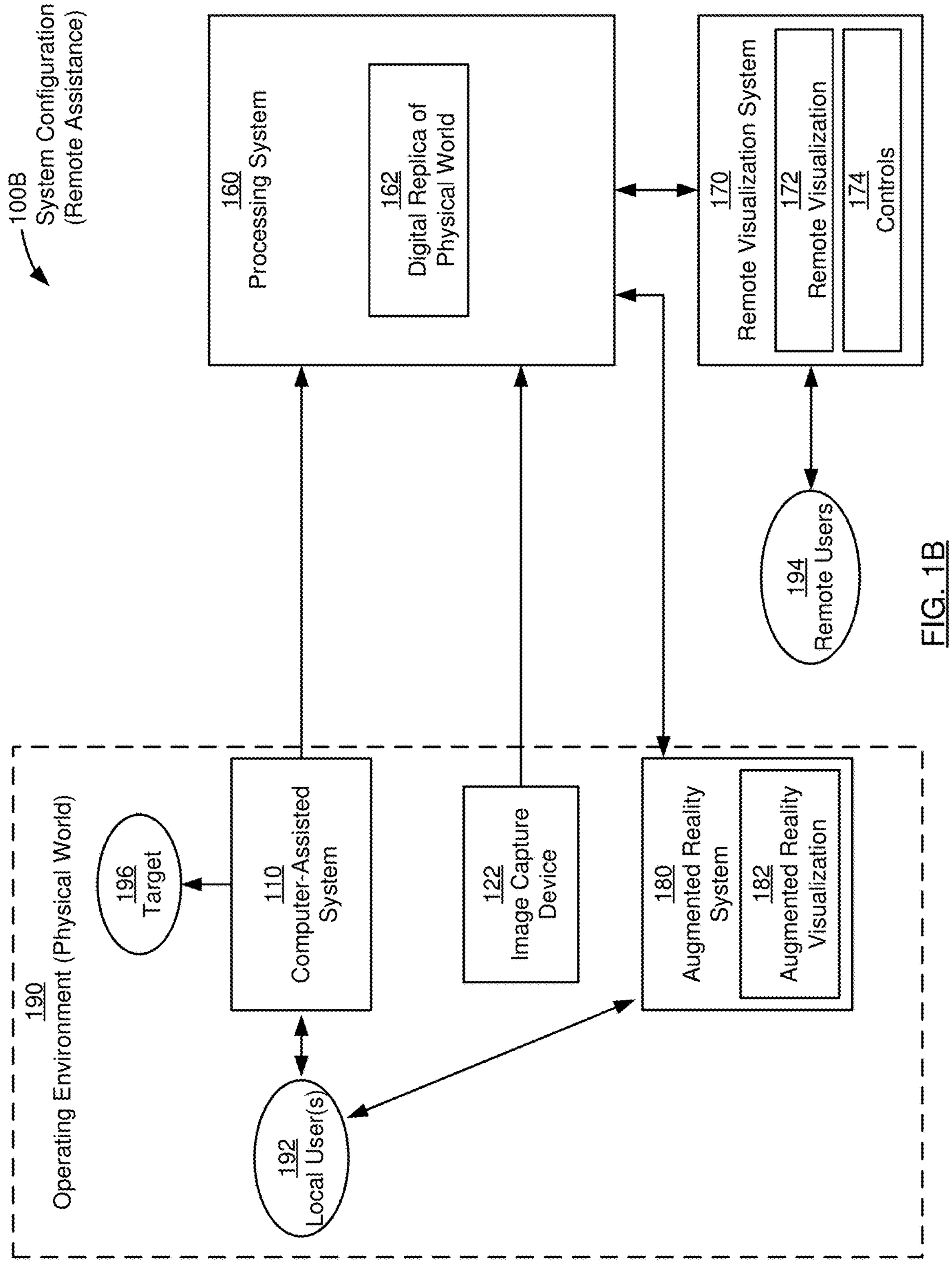
FIG. 1B shows a block diagram of a system configuration, in accordance with one or more embodiments.

Referring now to the drawings, in which like reference numerals represent like parts throughout the several views, FIG. 1A schematically shows a block diagram of a system configuration (100A), in accordance with one or more embodiments. The system configuration (100A) enables a content selection, in accordance with one or more embodiments. Other components are described in reference to FIG. 1B, showing a system configuration (100B) for remote assistance. The system of FIG. 1A and FIG. 1B may operate in conjunction to form a single system. More specifically, the system configuration (100B) for remote assistance may be used to present content that was selected using the system configuration (100A). The system configuration (100A) may include the computer-assisted system (110), and other components. The other components may form a coordination system (120) that coordinates content selection and/or presentation for use with the computer-assisted system (110) during a session, in accordance with one or more embodiments. During the session, the computer-assisted system (110) may interact with a target (196) in an operating environment (190) and may be operated by one or more users. The users may include local users (192) and/or remote users (194). The computer-assisted system (110) may include a computer-assisted medical system (such as a computer-assisted diagnostic system or a computer-assisted surgical system). The coordination system (120) may include a content selection engine (150). The coordination system (120) may further include a session awareness engine (130) and an image capture device (140). Each of these elements is subsequently described.

In one or more medical embodiments, the computer-assisted system (110) is a computer-assisted medical system as described below with reference to FIG. 2A and FIG. 2B, or any other type of medial system. Alternatively, in other medical embodiments the computer-assisted system (110) is a non-surgical computer-assisted medical system (such as a non-invasive, diagnostic system). Further, as another example, the computer-assisted system (110) may be a computer-assisted non-medical system (such as an industrial robot). The computer-assisted system (110) may be in an operating environment (190), i.e., an environment external to the computer-assisted system, such as a space surrounding or near the computer-assisted system. In a medical scenario, the operating environment (190) may be an examination room, an operating room, or some other medical setting. While not shown in FIG. 1A, the operating environment (190) may include additional components. For example, the operating environment (190) may include other objects, in addition to the computer-assisted system (110). The other objects may be physically separate from the computer-assisted system. Examples for other objects include, but are not limited to tables, cabinets, mayo stands, machinery, operator stations, supplies, other equipment such as machinery, humans, animals, supplies, etc.

In a medical example, the local user(s) (192) of the computer-assisted system (110) may be an operator of the computer-assisted system, an assistant, a service person, a student, a teacher, etc. In case of a computer-assisted medical system, a local user may be a healthcare professional operating the computer-assisted medical system (110). For a computer-assisted system (110) comprising a surgical system, the healthcare professional may be a surgeon or surgical assistant, a bedside assistant, a circulating nurse, etc. The local user(s) (192) may be located in the operating environment (190).

One or more of the local users (192) may benefit from the availability of content such as visual or auditory content. For example, a local user (192) may receive a video clip providing instructions for resolving a problem with the computer-assisted system (110). Different types of local users may benefit from different types of content. Accordingly, the type of local user to receive the content may be considered when selecting content by the content selection engine (150).

The remote user(s) (194) of the computer-assisted system (110) may include proctors, teachers, students, colleagues, collaborators, members of a support team, etc. Different remote users (194) may have different specializations. For example, remote users may be field personnel, technicians and engineers, robotics coordinators, field supervisors, and remote experts for the procedure being performed using the computer-assisted system (110). The remote user(s) (194) may be located outside the operating environment (190). The following paragraphs provide examples of types of remote users. The system configuration (100A) may involve other types of remote users, without departing from the disclosure.

A robotics coordinator (not shown) may be located at the site of the computer-assisted system (110) and be an employee of the institution owing and/or operating the computer-assisted system (110). The robotics coordinator may be trained in the basics of the computer-assisted system (110) and may help coordinate the use of the computer-assisted system (110).

A field technician (not shown) may be near the site of the computer-assisted system and may be potentially locally available at the site of the computer-assisted system (110). For example, the field technician may be an employee of a hospital operating a computer-assisted medical system. As another example, the field technician may not be immediately local, but close enough to arrive at the site within hours or days. The field technician may have limited general training and knowledge, and may be able to assist with common, basic technical support problems. The field technician may have received training by the manufacturer of the computer-assisted system (110).

A field supervisor (not shown) may be able to assist with technical problems that are beyond the knowledge of a typical field technician. A field supervisor may be able to be on-site within a reasonable time frame once support is requested, be on-call to provide remote support to the field technician or other field personnel, etc. A field supervisor may have received training by the manufacturer of the computer-assisted system (110).

A remote expert (not shown) may be able to assist with challenges of various types. For example, a remote technical expert may be able to assist with challenging technical problems with the computer-assisted system (110). In case of a computer-assisted medical system, a remote medical expert may be able to assist with challenges with a medical procedure, such as the complex workflows or other complexities of ongoing surgery. Different types of remote technical experts may be available. For example, some remote experts may assist with broad system-level knowledge, whereas other remote experts may assist with highly specific problem, for example problems related to a particular instrument, a particular procedure being performed with the computer-assisted medical system (110), etc.

Each of these remote users may benefit from the availability of certain types of content. Different types of remote users may benefit from different types of content. Accordingly, the type of remote user to receive the content may be considered when selecting content by the content selection engine (150).

The target (196), in a medical embodiment, may be an excised part of human or animal anatomy, a cadaver, a human, an animal, or the like. For example, in FIG. 2A, the target (196) is a patient (290) receiving medical tests or treatment through a procedure performed by the computer-assisted system (110). The target (196) may be any other object with which the computer-assisted system (110) can interact.

Continuing with the discussion of the coordination system (120), in one or more embodiments, the session awareness engine (130) is software, hardware, and/or a combination of software and hardware configured to determine a context (140). The session awareness engine (130) includes a set of machine-readable instructions (stored on a computer-readable medium) which, when executed by a computing device, perform one or more of the operations described in the flowcharts of FIG. 4A and FIG. 4B. The session awareness engine (130) may be implemented on a computing device of the computer-assisted medical system (110), such as the computing system described below with reference to FIG. 2B. The session awareness engine (130) may alternatively be hosted in a cloud environment or may be implemented on one or more remote computing devices including a remote computing device of the remote user (194). The session awareness engine (130) may include a system awareness engine (132) and an environment awareness engine (136)

The system awareness engine (132) may obtain parameters from the computer-assisted system (110). These parameters may include any information that provides insight into the current operational state of the computer-assisted system (110). For example, numerous parameters of a robotic manipulation system (as described below with reference to FIG. 2A and FIG. 2B), such as joint positions or velocities, type of tools or instruments, states of tools or instruments, control modes, etc., may be collected. Other parameters that may be collected include hardware serial numbers, firmware versions, installed hardware and/or software modules, error logs, etc.

The environment awareness engine (136) may obtain parameters from sources different from the computer-assisted system (110). For example, the environment awareness engine (136) may process data obtained from an image capture device (122) (which may be referred to as image data or just data) to extract additional information, beyond the system parameters of the computer-assisted system (110). In the medical example of FIG. 2A, the environment awareness engine (136) may detect whether a target (196) is already present for an upcoming operation, whether a component of the computer-assisted system (110) is inside or outside a sterile area, etc. The environment awareness engine (136) may further gather information from other sources. For example, the environment awareness engine (136) may query other types of sensors in the operating environment and/or external databases of information (e.g., hospital databases) and/or may generally obtain data and metadata from any connected devices (e.g., viewing devices), etc. Any information obtained from sources different from the computer-assisted system (110) may be considered by the environment awareness engine (136).

The parameters gathered by the system awareness engine (132) and the environment awareness engine (136) may be compiled to form the system-internal context (134) and/or system-external context (138), discussed in more detail below.

In one or more embodiments, the image capture device (122) is configured to capture images or sequences of images (videos) of the computer-assisted system (110) and/or the operating environment (190) external to the computer-assisted system. The image capture device (122) may, thus, provide image data suitable for determining context that cannot necessarily be obtained directly from data about the computer-assisted medical system (110) itself. For example, image data may be used to detect a state of the target (e.g., when the target (196) is a patient: if the patient is present, what the state of the patient is (patient prepped and/or under anesthesia, etc.)).

The image capture device (122) may capture two-dimensional or three-dimensional (3D) image data. The image capture device may include a 3D depth sensor operating based on time-of-flight principles or any other principle suitable for generating the 3D image data at the desired spatial and temporal resolution. The raw output of the image capture device (122), obtained at an instant in time, may be a 3D point cloud. Subsequent processing may produce an image frame that includes a 3D mesh, representing the captured operating environment (190). The image capture device (122) may be mounted either on a component of the computer-assisted medical system (110), or on a wall, a ceiling, etc. In one or more embodiments, the image capture device may be part of an augmented or mixed reality system worn by a local user (192). Head tracking may be integrated to enable registration of the captured image data with the computer-assisted system (110) and/or the operating environment of the computer-assisted system. As an alternative, or in addition to the image capture device (122), other types of operating environment sensors may be used. For example, one or more motion sensors, laser scanners, ultrasound scanners, etc. may be used. Sensors that are integrated with other equipment may also be used. For example, a sensor may be integrated into an operating table to detect presence or absence of the patient, one or more sensors may be integrated into an anesthesia cart to allow monitoring the state of anesthesia, etc.

The content selection engine (150) is software, hardware, and/or a combination of software and hardware configured to process the context (140) including the system-internal and/or system-external context (134, 138) in order to coordinate content selection and/or content presentation for one or more of the local users (192) and/or one or more of the remote users (194). The coordination of content selection and/or content presentation may occur for various scenarios. For example, a coordination of content selection and/or content presentation may be performed to facilitate remote assistance by a remote user (194) in response to a support request received from a local user (192). In this scenario, a content selection may be performed with the goal to provide the remote user (194) with the content (visual and/or auditory) needed to support the local user (192). A detailed discussion of various scenarios, including specific examples, is provided below. The content selection engine (150) includes a set of machine-readable instructions (stored on a computer-readable medium) which, when executed by a computing device, perform one or more of the operations described in the flowchart of FIG. 5. The content selection engine (150) may be implemented on a computing device of the computer-assisted system (110), such as the computing system described below with reference to FIG. 2B. In one or more embodiments, the content selection engine (150) is hosted in a cloud environment. Accordingly, a data network (not shown) may establish a connection between the system awareness engine (132), the environment awareness engine (136), and the content selection engine (150).

In one embodiment, the content selection engine (150) includes a content selection logic (152). The content selection logic (152) may process the system-internal context (134) and/or the system-external context (138) to identify a content for presentation to a local or remote user (192, 194), from a multitude of contents (198A-N). The content selection logic (152) may be configured to select content meeting the needs of the local or remote user (192, 194). A description of the content selection logic (152) is provided below with reference to the flowcharts. Specific examples of the content selection logic (152) are provided in FIG. 6A and FIG. 6B.

The multitude of contents (198A-198N) may include any type of content presentable to one or more local and/or remote users (192, 194). The multitude of contents (198A-198N) may include static content (e.g., documentation), and/or dynamic content (e.g., video and/or audio content that may be live). Each type of content may be obtained from a corresponding content source. For example, a live camera view may be obtained from a camera, a configuration view may be obtained from a database, etc. A few examples are subsequently provided. Some of these examples include elements that are described below, in reference to FIG. 1B and FIG. 2A.

(i) Preoperative data view: The preoperative data view may include, for example, 3D segmented models including anatomical visualizations for surgical planning. Preoperative data views may be derived from diagnostic CT images or other imaging data.

(ii) Point cloud view, mesh view: Image data obtained by the image capture device (122) may be three-dimensional (3D). The 3D image data may be obtained from the image capture device as a 3D point cloud. In subsequent steps, the 3D point cloud may be processed to obtain a 3D mesh, and an object detection may subsequently be performed.

(iii) System model view: The computer-assisted system (110) may be represented by a system model in a digital replica of the physical world. The system model of the computer-assisted system (110) may be a configurable digital representation such as a 3D model of the computer-assisted system (110) that may reflect the current state of the computer-assisted system in real-time or near real-time.

(iv) Endoscopic view: The computer-assisted system (110) may include an endoscope, e.g., when the computer-assisted system is a medical device. The endoscope may capture images of a worksite which may be provided to a user such as a surgeon.

(v) User control system view: The computer-assisted system (110) may include a user control system configured to enable a user to configure and administrate the computer-assisted system. The user control system view may include a system settings screen, an operating room configuration view (such as a room planner view that provides spatial info of objects inside the operating room), a procedure segmented view that provides a list of steps of the procedure to be performed, and/or a current state of the computer-assisted system.

(vi) Different types of camera views, (e.g., a first-person view by a user operating the computer-assisted system (110), a fixed camera in the operating environment (190), a bedside camera showing a patient, etc. Any camera view of the operating environment or parts of the operating environment may be considered.

Many other types of content (198A-N) may be available for selection by the content selection engine (150), without departing from the disclosure. For example, the content may include endoscope views, live camera views of the operating room, a doll house showing where users and/or objects are within the operating room, etc.

Examples for when these different types of content may be selected for presentation are provide below.

While not explicitly shown in FIG. 1A, at least some of the components involve a computing system. For example, the session awareness engine (130) and the content selection engine (150) may execute on one or more computing systems. The computing system(s) may be similar to the computing system(s) described in reference to FIG. 2B.

Turning to FIG. 1B a block diagram of a system configuration (100B), in accordance with one or more embodiments, is schematically shown. The system configuration (100B) is for providing remote assistance, in accordance with one or more embodiments.

Remote presentation or interaction can be used to support collaboration, training, communication, and other objectives of presentation or interaction. Remote presentation or interaction can also be used to support a local user of a computer-assisted system by a remote user (for example, a remote support person), or vice versa. The remote user may be provided with a remote visualization of the computer-assisted system (e.g., a computer-assisted robotic and/or medical system), the operating environment, and/or other components, enabling the remote user to view and visually inspect the computer-assisted robotic and/or medical system, the operating environment, and/or other components, for example, to detect and/or analyze a problem, or to learn. The content that the remote user may want to receive or should receive may depend on the current context, as previously discussed in reference to FIG. 1A. Accordingly, in one or more embodiments, the content to be presented to the remote user may be selected by the content selection engine (150), introduced in FIG. 1A. The subsequent discussion introduces the system configuration (100B) for providing remote assistance, followed by a discussion of the use of the system configuration (100B) in conjunction with the system configuration (100A) to provide content to the remote user, after selecting the content.

The system configuration (100B) for providing remote assistance may include the computer-assisted system (110), and other components that enable the remote assistance. The system configuration (100B) may enable interaction between one or more local users (192) and one or more remote users (194). The interaction may be local between local users (192) and/or remote between one or more local users (192) and one or more remote users (194). The interaction may be provided to support the local users (192), to provide learning opportunities for the local and/or remote users (192, 194), or to provide any other interaction-related objective, such as when operating the computer-assisted system (110) in the operating environment (190).

In addition to the components described in reference to FIG. 1A, the system configuration (100B) includes components such as the processing system (160), the remote visualization system (170), and the augmented reality system (180), as described below.

In one or more embodiments, the processing system (160) includes software, hardware, and/or a combination of software and hardware forming various components (not shown) such as an image processing engine, a modeling engine, one or more rendering engines, etc. These components may be configured to obtain image frames from the image capture device (122), based on the image frames, generate a digital replica (162) (further discussed below) of the physical world and use the digital replica (162) to render content in different ways for presentation to local users (192) via the augmented reality system (180) and remote users (194) via the remote visualization system (170), as discussed below.

The digital replica (162) of the physical world, in one or more embodiments, is a digital representation of the operating environment (190), of the computer-assisted system (110), and/or of one or more objects that may exist in the operating environment. The digital replica (162) may be used as a medium to establish a shared understanding between the local user(s) (192) and the remote user(s) (194). The digital replica (162) may, thus, be used to facilitate various support tasks. More specifically, the digital replica may be used as a medium to facilitate assistance to a local user (192) of the computer-assisted system (110), by a remote user (194). A remote visualization of the computer-assisted system (110) in its operating environment (190) may be derived from the digital replica (162) and may be provided to the remote user (194). The remote user (194) may rely on the remote visualization to remotely examine the computer-assisted system (110), an issue with the computer-assisted system (110), the operating environment (190), etc. The remote user (194) may annotate elements of the digital replica (162) to provide instructions to the local user (192). As discussed below, the digital replica (162) provides a shared spatial model for both the augmented reality (AR) visualization (182) for the local user (192) and the remote visualization (172) for a remote user (194), although different aspects of the digital replica (162) are relied upon by the AR visualization (182) and the remote visualization (172).

Broadly speaking, the image frames from the image capture device (122) may undergo computer vision operations, for example, to identify objects such as the computer-assisted system (110). To obtain the digital replica (162), the computer-assisted system (110) and/or other identified objects may be replaced with corresponding configurable system models. The configurable system model of the computer-assisted system (110) may be a configurable digital representation such as a 3D model of the computer-assisted system (110). In one or more embodiments, the configurable elements of the system model include a kinematic configuration. Assume, for example, that the computer-assisted system (110) is a robotic manipulation system. The kinematic configuration may apply to the robotic manipulation system. The kinematic configuration may further apply to a user control system and/or other components associated with the computer-assisted system. Examples of these components are described below with reference to FIG. 2A and FIG. 2B. Joint positions and/or orientations may be used to specify parts of the kinematic configuration or the entire kinematic configuration. Other configurable elements may include, but are not limited to, indicator lights (color, status (blinking vs constant), status displays, sound emitters (beeps, messages) of the computer-assisted system (110), etc. Object models (not shown), representing objects (not shown) in the operating environment may be processed in a similar manner.

The system model may be periodically updated to have the system model reflect a current configuration (e.g., the current kinematic configuration) of the actual computer-assisted system (110) in the physical world.

The remote visualization system (170), in one or more embodiments, includes a display allowing a remote user (194) to see a remote visualization (172) of the physical world. The remote visualization (172) may be based on the digital replica (162) and may include a rendering of the operating environment (190), the system model of the computer-assisted system (110), and/or other components in the operating environment (190). The rendering of the operating environment may be based on the 3D point cloud or the 3D mesh, obtained by processing the data obtained from the image capture device (122). What components of the digital replica (162) are rendered in the remote visualization (172) may be user-selectable and/or may be determined based on operations performed by the content selection engine (150). For example, the remote user (194) may choose to limit the remote visualization (172) to include the system model with or without the rendering of the operating environment (190). The remote visualization system (170) may include controls (174) that may enable the remote user (194) to navigate within the remote visualization (172), e.g., by zooming, panning, etc. Further, the controls (174) may enable the remote user (194) to annotate components displayed in the remote visualization (172).

The augmented reality system (180), in one or more embodiments, is a system that enables a local user (192) to see the physical world of the operating environment (190) enhanced by additional perceptual information.

An augmented reality (AR) visualization (182) for a local user (192) may be derived from the digital replica (162). The AR visualization (182) may be viewed, for example, using an augmented reality (AR) display on AR glasses, a separate monitor, or some other display. In the augmented reality visualization, the annotations provided by the remote user may be superimposed on the actual, physical elements seen through the AR glasses. The annotations may include any appropriate visual item; for example, an annotation may contain text, markers, direction arrows, labels, other textual or graphical elements that may be static or animated, that may be used to telestrate, annotate, entertain, or provide any other visual interaction function. The annotations may be provided based on input provided by the remote user (194). For example, an annotation may identify or point out a particular component of the computer-assisted system (110) by including a marker or label in the AR visualization (182) that is superimposed on the component to be pointed out. The annotations may include content selected by the content selection engine (150), as further discussed below.

Spatial alignment of the annotations and the physical elements is accomplished by obtaining or maintaining a spatial registration between the digital replica and the physical world, e.g., in presence of user movement.

The AR system (180) may also be based on technologies different from AR glasses. For example, instead of enabling a local user (192) to perceive the physical world of the operating environment (190) through transparent or semi-transparent glasses, the AR visualization (182) may provide a captured image of the physical world using one or more displays. A camera image of the physical world may be shown in the display (which may include a fixed display (e.g., a monitor), a moveable display (e.g., a tablet computer), and/or a wearable display (e.g., a head mounted display), and the sub-images may be added directly to the image in the display.

While not explicitly shown in FIG. 1B, at least some of the components involve a computing system. For example, the processing system (160), the remote visualization system (170) and the augmented reality system (180) may execute on one or more computing systems. The computing system(s) may be similar to the computing system(s) described in reference to FIG. 2B.

Further, while FIG. 1A and FIG. 1B show certain components at certain locations, those skilled in the art will recognize that the disclosure is not limited to this particular configuration. For example, while a distinction is made between local users (192) and remote users (194), the remote users (194) may or may not be far away from the local users (192). A remote user (194) may be in a same room but not in the same vicinity as a local user (192) (in a surgical example, the local user may be sterile personnel able to enter the sterile space, while the remote user may be non-sterile personnel keeping outside of the sterile space), be in the same facility but in a different room from the operating environment, be in a different facility, be in a different country, or anywhere else, e.g., on a different continent. In some scenarios, there may not be a remote user (194) at all. Similarly, while components are shown as arranged in a particular manner, these components may be arranged differently, without departing from the disclosure. For example, some components may be located in whole or in part anywhere, e.g., in the operating environment, in a cloud environment, or combined with the remote components. At least some of the components may also be distributed.

Figure 2A:
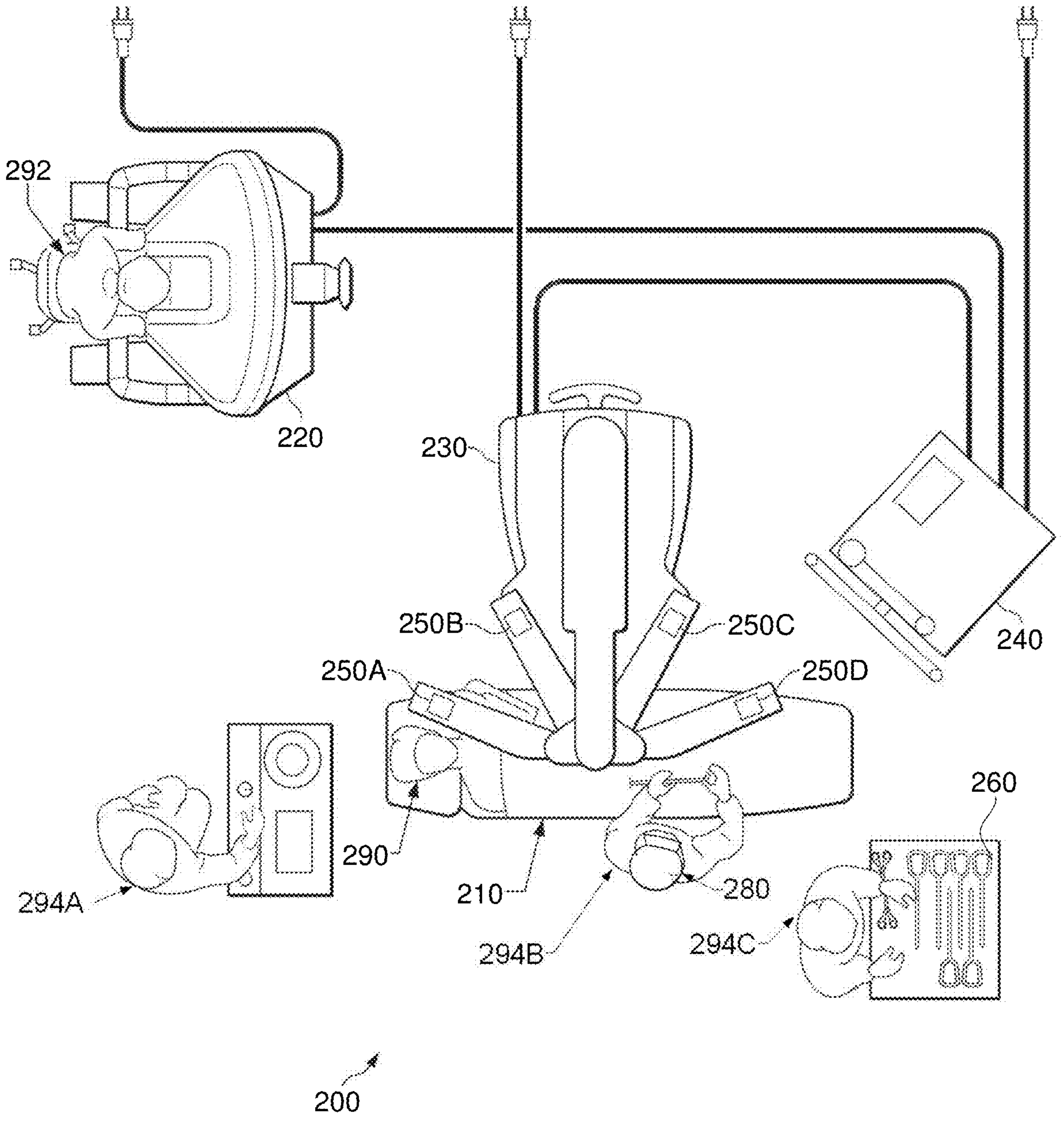
FIG. 2A shows an overhead view of a computer-assisted medical system in a robotic procedure scenario, in accordance with one or more embodiments.

FIG. 2A shows an overhead view of a computer-assisted medical system (200) in a robotic procedure scenario. The components shown in FIG. 2A may be located in the operating environment (190) of FIG. 1A and FIG. 1B. The computer-assisted medical system (200) may correspond to the computer-assisted system (110) of FIG. 1A and FIG. 1B. While in FIG. 2A, a minimally invasive robotic surgical system is shown as the computer-assisted medical system (200), the following description is applicable to other scenarios and systems, e.g., non-surgical scenarios or systems, non-medical scenarios or computer-assisted systems, etc.

In the example, a diagnostic or surgical procedure is performed on a patient (290) placed on an operating table (210). The system may include a user control system (220) for use by an operator (292) (e.g., a clinician such as a surgeon) during the procedure. One or more assistants (294A, 294B, 294C) may also participate in the procedure. The computer-assisted medical system (200) may further include a robotic manipulating system (230) (e.g., a patient-side robotic device) and an auxiliary system (240). The robotic manipulating system (230) may include at least one manipulator arm (250A, 250B, 250C, 250D), each of which may support a removably coupled instrument (260) (also called instrument (260)). In the illustrated procedure, the instrument (260) may enter the body of the patient (290) through a natural orifice such as the throat or anus, or through an incision, while the operator (292) views the worksite (e.g., a surgical site in the surgical scenario) through the user control system (220). An image of the worksite may be obtained by an imaging device (e.g., an endoscope, an optical camera, or an ultrasonic probe), i.e., an instrument (260) used for imaging the worksite, which may be manipulated by the robotic manipulating system (230) so as to position and orient the imaging device.

The auxiliary system (240) may be used to process the images of the worksite for display to the operator (292) through the user control system (220) or other display systems located locally or remotely from the procedure. Based on the images provided to the operator (292), the operator may control one or more instruments (260) at the worksite. The user control system (220) may be equipped with one or more input devices (not shown) such as haptic manipulanda, which the operator (292) may control using his or her hands. Operation of the input devices by the operator (292) may cause movement of the instruments (260). The number of instruments (260) used at one time generally depends on the task and space constraints, among other factors. If it is appropriate to change, clean, inspect, or reload one or more of the instruments (260) being used during a procedure, an assistant (294A, 294B, 294C) may remove the instrument (260) from the manipulator arm (250A, 250B, 250C, 250D), and replace it with the same instrument (260) or another instrument (260).

In FIG. 2A, the assistant (294B) wears AR glasses (280) of the AR system (180), introduced in FIG. 1B.

Figure 2B:
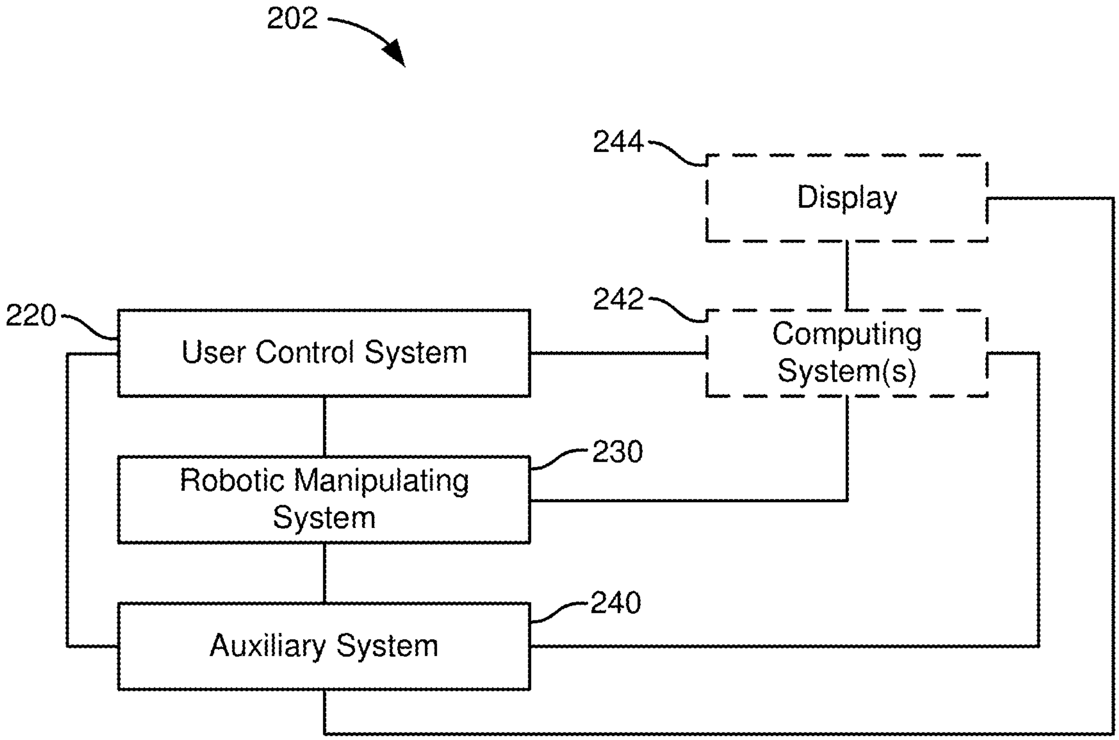
FIG. 2B diagrammatically shows various components of the robotic procedure scenario of FIG. 2A, in accordance with one or more embodiments.

FIG. 2B provides a diagrammatic view (202) of the computer-assisted medical system (200). The computer-assisted medical system (200) may include one or more computing systems (242). The computing system (242) may be used to process input provided by the user control system (220) from an operator. A computing system may further be used to provide an output, e.g., a video image to the display (244). One or more computing systems (242) may further be used to control the robotic manipulating system (230).

A computing system (242) may include one or more computer processors, non-persistent storage (e.g., volatile memory, such as random-access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (242) may be an integrated circuit for processing instructions. For example, the computer processor may be one or more cores or micro-cores of a processor. The computing system (242) may also include one or more input devices, such as a touchscreen, keyboard, mouse, microphone, touchpad, electronic pen, or any other type of input device.

A communication interface of a computing system (242) may include an integrated circuit for connecting the computing system (242) to a network (not shown) (e.g., a local area network (LAN), a wide area network (WAN) such as the Internet, mobile network, or any other type of network) and/or to another device, such as another computing system (242).

Further, the computing system (242) may include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

A computing system (242) may be connected to or be a part of a network. The network may include multiple nodes. Each node may correspond to a computing system, or a group of nodes. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system may be located at a remote location and connected to the other elements over a network.

The robotic manipulating system (230) may use an instrument (260) including an imaging device, e.g., an endoscope or an ultrasonic probe, to capture images of the worksite and output the captured images to an auxiliary system (240). The auxiliary system (240) may process the captured images in a variety of ways prior to any subsequent display. For example, the auxiliary system (240) may overlay the captured images with a virtual control interface prior to displaying the combined images to the operator via the user control system (220). The robotic manipulating system (230) may output the captured images for processing outside the auxiliary system (240). One or more separate displays (244) may also be coupled with a computing system (242) and/or the auxiliary system (240) for local and/or remote display of images, such as images of the procedure site, or other related images.

Figure 3:
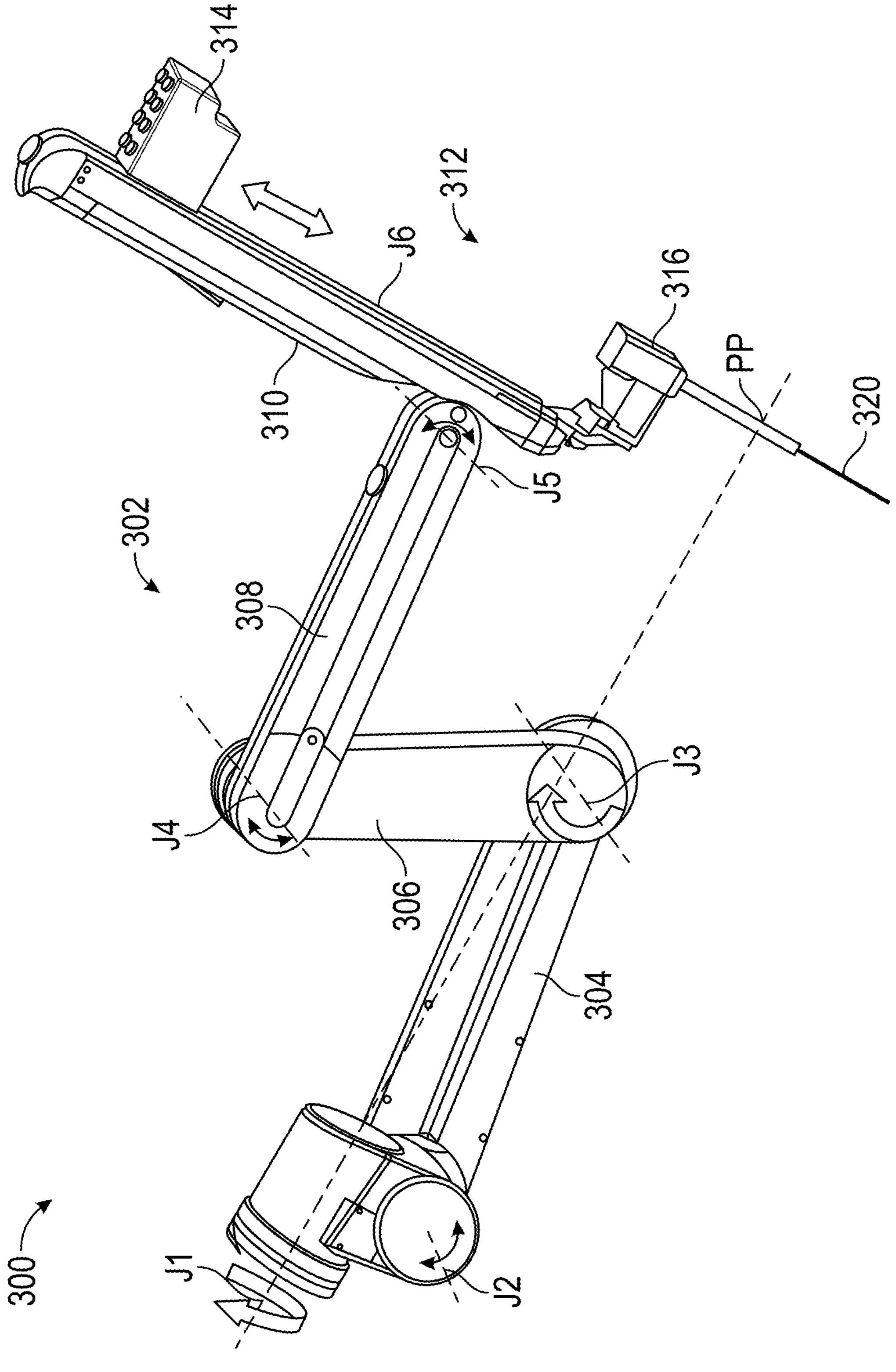
FIG. 3 shows an example of a manipulator arm assembly, in accordance with one or more embodiments.

An example of a manipulator assembly (300) in accordance with embodiments of the disclosure is shown in FIG. 3. A manipulator assembly (300) may include a manipulator arm (302) and a tool (320) (also called instrument (320)) (in FIG. 3, only an axis of the instrument, but not the instrument itself, is shown). The manipulator arm (302) may correspond to the manipulator arm (250A, 250B, 250C, 250D) in FIG. 2B. As described above, during operation, the manipulator arm (302) generally supports a distal instrument or tool (320) and effects movements of the instrument (320).

In minimally invasive scenarios, an instrument (320) may be positioned and manipulated through incisions in the patient so that a kinematic remote center is maintained at the incision so as to minimize the size of the incision or forces applied to tissue surrounding the incision. More specifically, an elongate shaft of an instrument (320) allows the end effectors and the distal end of the shaft to be inserted distally into a worksite through a lumen of the cannula often inserted through a body wall such as an abdominal wall. The worksite may be insufflated. Images of the worksite, taken by an imaging tool such as an endoscope, may include images of the distal ends of the instruments or tools (320) when the instruments (320) are positioned within the field-of-view of a tool operating as an imaging device.

As a number of different instruments (320) having differing end effectors may be sequentially mounted on a manipulator arm (302), or as an instrument (320) needs to be removed and reinstalled during a procedure, a distal instrument holder facilitates removal and replacement of the mounted instrument or tool.

As may be understood with reference to FIG. 2A, manipulator arms (302) are proximally mounted to a base of the robotic assembly. In one or more embodiments, manipulator arms (302) may be mounted to separate bases that may be independently movable, e.g., by the manipulator arms (302) being mounted to single-manipulator-arm carts, being provided with mounting clamps that allow mounting of the manipulator arms (302) directly or indirectly to the operating table (shown in FIG. 2A) at various locations, etc. Typically, a manipulator arm (302) includes a plurality of manipulator arm segments and associated joints extending between the proximal base and the distal instrument holder.

In embodiments such as shown for example in FIG. 3, a manipulator arm includes multiple joints (such as revolute joints J1, J2, J3, J4, and J5, and prismatic joint J6) and links or manipulator arm segments (304, 306, 308, and 310). The joints of the manipulator arm, in combination, may or may not have redundant degrees of freedom. A manipulator arm with one or more redundant degrees of freedom has a plurality of joints such that the plurality of joints may be driven into a range of differing configurations for a given position and orientation of a portion of the manipulator arm. For example, a manipulator arm with one or more redundant degrees of freedom may have a plurality of joints that may be driven into a range of differing configurations for a given position and orientation of a distal portion or end effector of the manipulator arm. For example, the manipulator arm (302) of FIG. 3 may be maneuvered into differing configurations while the distal member (312) supported within the instrument holder (310) maintains a particular state and may include a given position or velocity of the end effector. The instrument holder (310) may include a cannula (316) through which the instrument shaft of the instrument (320) extends, and the instrument holder (310) may include a carriage ((314) shown as a box-shaped structure that translates on a spar) to which the instrument attaches before extending through the cannula (316) toward the worksite.

Actuation of the degrees of freedom of the instrument (320) is often provided by actuators of the manipulator. These actuators may be integrated in the carriage (314). A distal wrist of the instrument may allow pivotal and/or linear motion of an end effector of the instrument (320) about instrument joint axes of one or more joints at the instrument wrist. An angle between end effector jaw elements may be controlled independently of the end effector location and orientation.

In FIG. 3, when the instrument (320) is coupled or mounted on the manipulator arm (302), the shaft extends through the cannula (316). The instrument (320) typically is releasably mounted on an instrument holder (310) of the manipulator arm (302), which may be driven to translate along a linear guide formed by prismatic joint (J6). This may also be referred to as the "IO", and provide in/out movement along an insertion axis.

While FIG. 2A, FIG. 2B, and FIG. 3 show various configurations of components, other configurations may be used without departing from the scope of the disclosure. For example, various components may be combined to create a single component. As another example, the functionality performed by a single component may be performed by two or more components. Further, while the components are often described in the context of surgical scenarios, embodiments of the disclosure are applicable to medical scenarios outside of surgery, and to other non-medical domains that involve robotic manipulation. In addition, embodiments of the disclosure may involve different types of computer-assisted robotic systems. For example, while the manipulator arm (302) is rigid, other embodiments may include flexible robotic devices such as steerable flexible catheters.

Figure 4A:
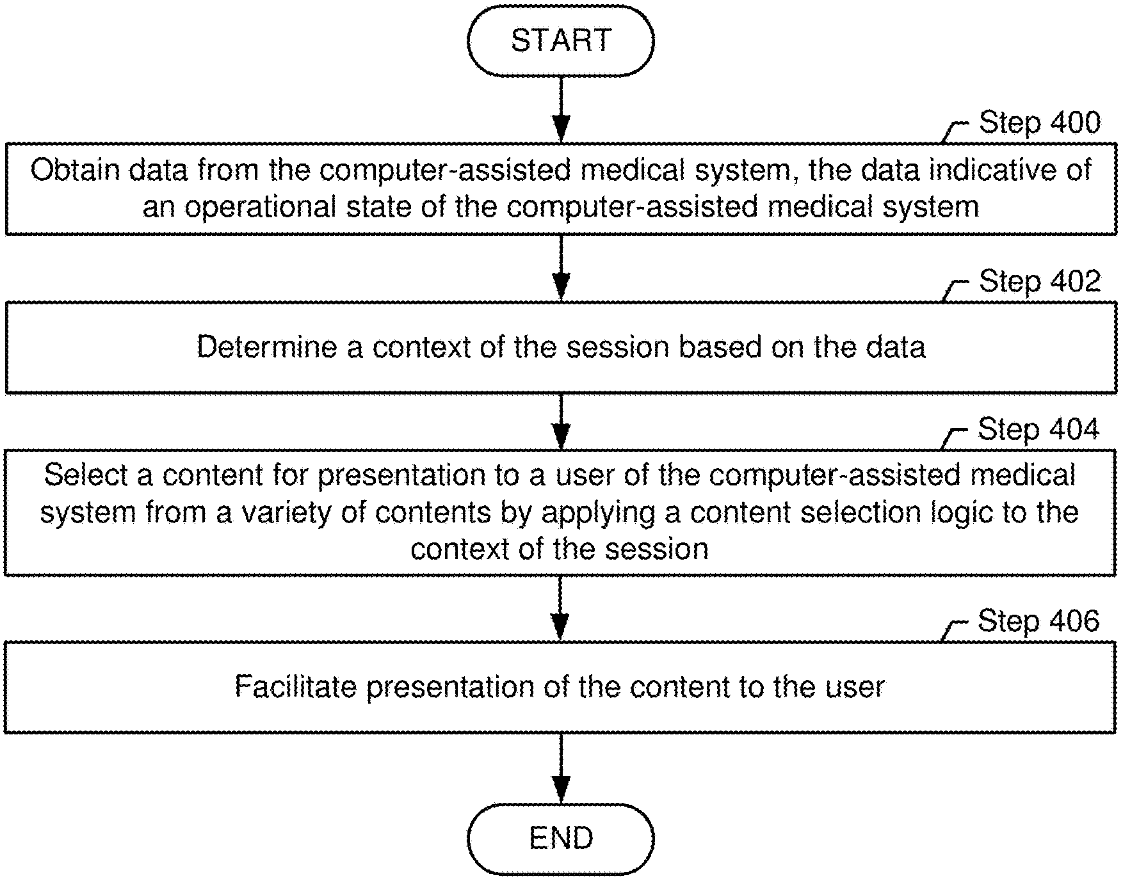
FIG. 4A and FIG. 4B show a flowchart describing coordinating content presentation associated with a session involving use of a computer-assisted medical system, in accordance with one or more embodiments.
Figure 4B:
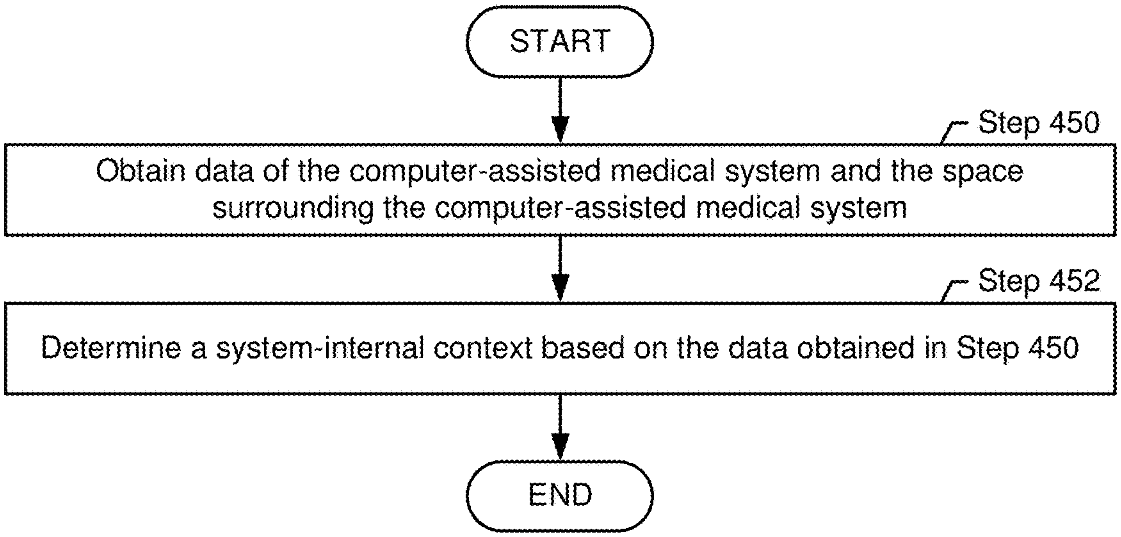
Figure 5:
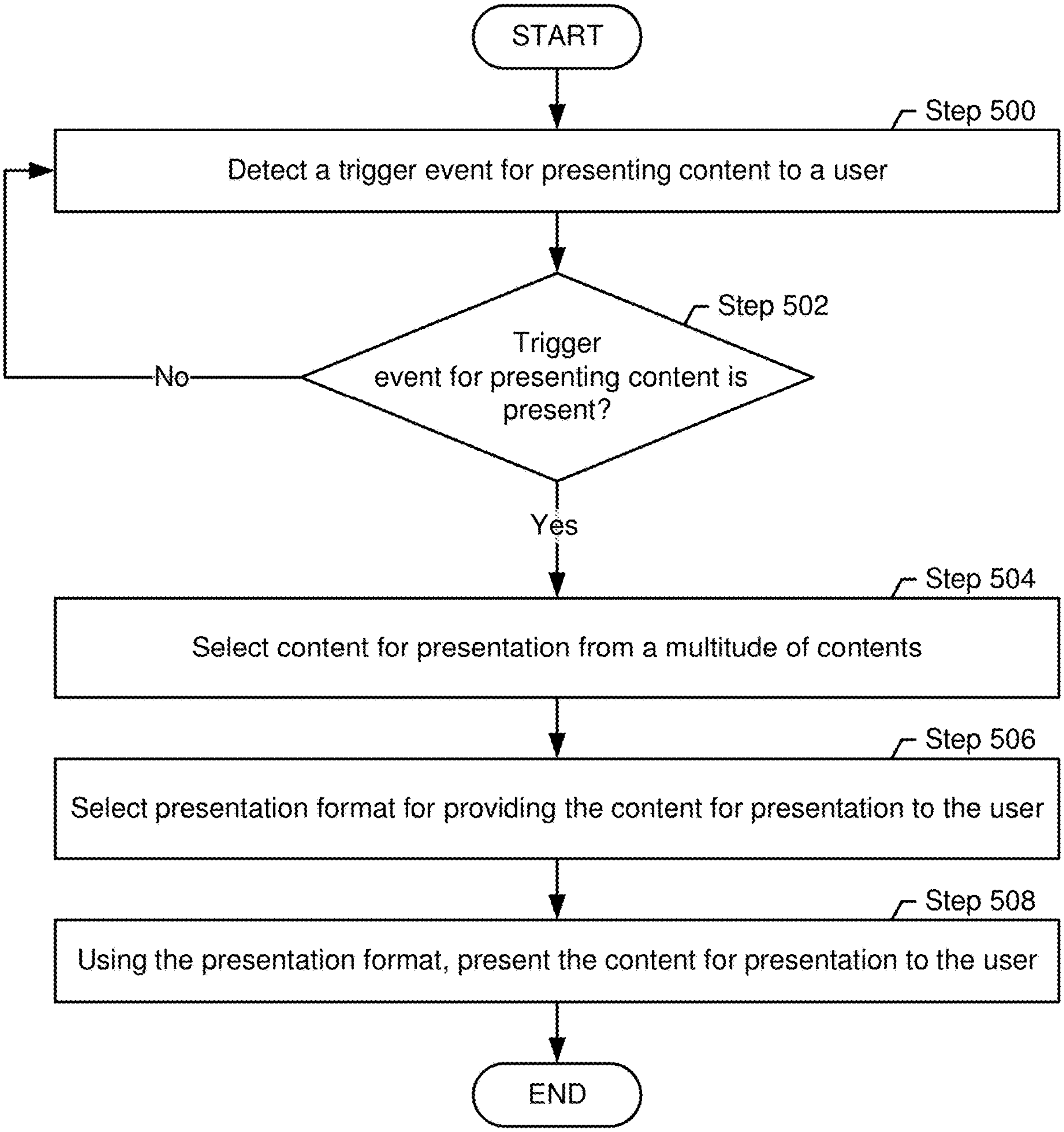
FIG. 5 shows a flowchart describing methods for coordinating content presentation, in accordance with one or more embodiments.

Turning to the flowcharts, FIG. 4A, FIG. 4B, and FIG. 5 depict methods for coordinating content presentation in assisted systems, in accordance with one or more embodiments. One or more of the steps in FIG. 4A, FIG. 4B, and FIG. 5 may be performed by various components of the systems, previously described with reference to FIG. 1A, FIG. 1B, FIG. 2A, FIG. 2B, and FIG. 3. Some of these figures describe particular computer-assisted medical systems. However, the subsequently described methods are not limited to a particular configuration of a computer-assisted medical system. Instead, the methods are applicable to any type of computer-assisted medical system or, more generally, any type of computer-assisted robotic system.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 4A, FIG. 4B, and FIG. 5.

FIG. 4A and FIG. 4B describes how a context (including a system-internal and/or a system-external context) is obtained in various embodiments for a session involving the use of the computer-assisted medical system. FIG. 5 describes how a content selection may be performed to facilitate a presentation of the selected content. The selection may be performed under consideration of the system-internal and/or system-external context.

Turning to FIG. 4A and FIG. 4B, a flowchart describing methods for obtaining a context, in accordance with one or more embodiments, is shown. The methods of FIG. 4A and FIG. 4B may be repeatedly executed to ensure that the context is up to date at any time.

In Step 400, data is obtained from the computer-assisted medical system where the data is indicative of the operational state of the computer-assisted medical system. The data obtained from the computer-assisted medical system may include parameters or any other information that provides insight into the current operational state of the computer-assisted medical system. For example, numerous parameters of a robotic manipulation system (as described below with reference to FIG. 2A, FIG. 2B, and FIG. 3), such as a kinematic configuration of the manipulator arm(s) and/or the instrument(s), types of instruments being mounted on the manipulator arm(s), the kinematic configuration of the instruments, activated control modes, the docking state of the cannula(s), whether the robotic manipulation system is powered, whether instruments are connected and what types of instruments are being used, whether the operator is engaged with the user control system, etc., may be collected. Other parameters that may be collected may include hardware serial numbers, firmware versions, installed hardware and/or software modules, errors of the computer-assisted medical system stored in error logs (e.g., errors associated with failed manipulator arms, errors associated with colliding manipulator arms, errors or warnings associated with range of motion issues, errors associated with failed manipulator arm-instrument engagements), etc. Any type of information may be collected from the computer-assisted medical system to determine the operational state of the computer-assisted medical system.

In Step 402, a context of a session is determined based on the data of the computer-assisted medical system. In addition or alternatively, the space surrounding the computer-assisted medical system is collected from data sources different from the computer-assisted medical system itself. For example, image data of the computer-assisted medical system and the operating environment external to the computer-assisted medical system (such as space surrounding or near the computer-assisted medical system) may be obtained. The obtained image data may be a single image frame, or a series of image frames (e.g., a video). Other types of data may be obtained from other sources such as other types of sensors in the operating environment, external databases of information (e.g., hospital databases), metadata from connected devices (e.g., viewing devices), etc.

In Step 404, a content for presentation to a user is selected from the contents by applying a content selection logic to the context of the session as described below. In Step 406, the presentation of the content to the user is facilitated such that the user is able to observe and/or use the content.

Turning to FIG. 4B, in Step 450, data of the computer-assisted medical system and the space surrounding the computer-assisted medical system is obtained using common techniques.

In Step 452, a system-internal context may be determined based on the data obtained in Step 450. The system-internal context may be based on the parameters that describe the operational state of the computer-assisted medical system. Accordingly, determining the system-internal context may involve various steps performed on the operational state of the computer-assisted medical system, as determined in Step 400. For example, the parameters describing the operational state may have been received in a raw machine data format. Determining the system-internal context may involve identifying and extracting the parameters of interest from the raw machine data. Additional steps may be performed. For example, certain values and/or flags may be evaluated to determine the system-internal context. The operations of Step 452 may be performed by rule-based algorithms and/or by machine learning algorithms. In one or more embodiments, the obtained parameters are further processed to derive additional system-internal context. For example:

(i) Based on a current kinematic configuration and a location of a patient (if known), it may be estimated whether the robotic manipulation system is currently in a use state, in a setup state before or after use, and/or whether elements of the robotic manipulation system are in proximity of the patient or not.

(ii) Based on a detection of the operator engaging with the user control system (e.g., by detecting the operator's head at a display viewer of the user control system), it may be estimated that the operator is taking control of the instrument(s) of the robotic manipulation system.

(iii) For systems using cannulas, based on whether a cannula is docked to a manipulator arm, it may be estimated whether a procedure is in progress (no cannula docked), or whether the robotic manipulation system is being set up or underway (cannula docked). When a cannula is docked, some systems may be programmed to assume that the robotic manipulation system is physically in contact and/or interacting with the patient.

(iv) Based on a mounting state (indicating whether the instrument is attached to the manipulator arm) and/or an insertion position along an insertion axis of an instrument, it may be estimated whether the instrument is extending into the patient anatomy.

(v) Based on a current type of an instrument being used, the type and/or state of a procedure currently being performed may be estimated. For example, while a scalpel may be used during an ongoing medical procedure, a needle driver may be used toward the end of the medical procedure.

(vi) Based on a current configuration of the instrument (e.g., forceps open versus closed), it may be estimated whether the instrument is currently grasping tissue or is interacting with the tissue in a different manner.

(vii) Based on the robotic manipulation system being or having been in teleoperation mode it may be estimated that a procedure is ongoing.

Broadly speaking, as illustrated by the examples (i)-(vii), an operational state of the robotic manipulation system may be estimated based on parameters obtained from the robotic manipulation system itself. Over time, a history of states may be established, reflecting the procedure that has been/is being performed using the robotic manipulation system. Those skilled in the art will appreciate that the estimation of the system operational state is system-specific and application-specific and is not necessarily universally valid. For example, if for one medical scenario it is known that the use of a particular forceps is uniquely associated with a very specific step being performed, it may be reasonable to predict that the specific step is being performed when the forceps is actually present. The same assumption may be not be valid for other medical scenarios. For example, in other medical scenarios, the forceps may be used in different steps or may not be used at all. The examples (i)-(vii) are associated with different risks and may require a different response, in case of a support request. While not specifically discussed, other additional information may be derived by analyzing the parameters obtained from the computer-assisted medical system, without departing from the disclosure.

In one or more embodiments, a system-external context is determined. The system-external context may be based on data obtained from data sources different from the computer-assisted medical system itself. Some system-external context may also be determined based on data obtained from the computer-assisted medical system. In one embodiment, the system-external context is determined based on image data. Digital image processing may be performed to detect elements that are present in the image frame(s). The digital image processing may operate on the image frame(s) provided by an image capture device in the operating environment. If the image data includes 3D image frames, the image frames may include point clouds or 3D meshes. In the example of the computer-assisted medical system of FIG. 2A, FIG. 2B, and FIG. 3, elements that may be detected include, but are not limited to, the robotic manipulation system, the operating table, the patient on the operating table, a sterile field, the presence of additional relevant components such as an anesthesia cart, the position of the robotic manipulation system relative to the operating table, etc.

The elements isolated by the image processing characterize aspects of the system-external context and provide information about the operational context of the system that is derived from observations made outside of the system. For example:

(i) Based on a presence or absence of a patient on the operating table (e.g., a patient-location state), the state or phase of a planned or ongoing procedure may be estimated: when no patient is present, the computer-assisted robotic system is not in an operation state, whereas when a patient is present, it is more likely that the computer-assisted robotic system is about to be used, being used, or was just used for a procedure. Additional indications of a procedure that is about to be performed, or an ongoing procedure, include the detection of a sterile field after the patient having been prepped (e.g., a patient preparation state), and/or the detection of an incision (e.g., an incision-made state). In addition, the type of the medical procedure being performed may be obtained, and information about the patient on which the medical procedure is performed may be obtained, for example, from databases.

(ii) Based on a presence of elements of the computer-assisted robotic system within the sterile field, it may be estimated that a procedure is ongoing, and that precautions may be necessary due to the possibility of interaction between the computer-assisted robotic system and the patient.

(iii) Additional system-external context may be obtained by identifying the persons that are present, such as whether a surgeon or other clinician, assistants, etc. are in the vicinity of the computer-assisted medical system. The identification may be based on the image data and/or other sources, e.g., when a user is logged on to a computer system using a user profile). In addition, their level of experience (if accessible by the environment awareness engine, for example, by retrieving information about the personnel from a database) may also be considered system-external context. The identification of persons may also include determining a spatial location of the persons in the operating environment. The detection of persons that are present may also include remote users and their role, which may define the type of the telepresence event (e.g., remote proctoring, remote mentoring, remote case observation, remote technical support, etc.).

More broadly, system-external context may be obtained from image data or from any other source. Generally, the system-external context may include any information that is not directly obtainable from the robotic manipulation system itself. As illustrated by the examples (i)-(iii), an operational state of the robotic manipulation system may be estimated based on parameters that are not directly obtainable from the robotic manipulation system itself, but that are instead gathered through monitoring of the operating environment external to the robotic manipulation system. Over time, a history of states may be established, reflecting the procedure that has been/is being performed using the robotic manipulation system. The system-external context, thus, broadens the scope of the available context to be used for controlling content presentation to users, remote or local, of the robotic manipulation system. While the above examples illustrate system-external context based on image processing, other system-external context may be relied upon as an alternative or in addition. For example, sensors built into the patient table or into the anesthesia cart, databases, etc. may provide additional system-external context.

The system-external context may be further be determined based on any type of data obtained from the computer-assisted medical system itself. For example, the presence of a particular person in the operating room, e.g., the surgeon operating the medical device, may be determined based on a parameter obtained from the computer-assisted medical system.

Similar to the determining of the system-internal context, determining the system-external context may involve various steps performed on the data obtained and used in Step 402, and possibly Step 400.

After the execution of the method of FIG. 4A or FIG. 4B, system-internal and/or system-external context is available and support the execution of the method of FIG. 5.

Turning to FIG. 5, a flowchart describing methods for coordinating content presentation, in accordance with one or more embodiments, is shown. Broadly speaking, the method may include a step to determine that a presentation of content to a user of the computer-assisted system is necessary or desirable. In a next step, content that is considered suitable is selected under consideration of the system-internal and/or system-external context. Subsequently, the selected content may be provided to the user. The steps of the flowchart may be executed at any time. For convenience, the examples below are for when the computer-assisted system, is a computer-assisted medical system.

In Step 500, a trigger event for presenting content to a user may be detected. The trigger event may be an explicit request by the user (e.g., a support request submitted by a user), or any other trigger event such as a condition being met. A support request may be received from a user of the computer-assisted medical system.

In one or more embodiments of the invention, the trigger event may be implicit. In this case, the trigger event may be a result of one or more conditions being met. A trigger event may be a result of a particular context or a change of the context. For example, a trigger event may be a specific error condition of the computer-assisted medical system, a telepresence session being started, etc. In one embodiment, there is no trigger event. In other words, the trigger event is optional, and content may be continually presented and updated as the context changes.

Different frameworks may be used to detect the presence of a trigger event. For example, the system-internal and/or system-external context may be evaluated using one or more conditional statements such as IF-THEN statements.

In Step 502, if a trigger event is determined to be present, the method may proceed with the execution of Step 504. If not trigger event is detected, the method may return to Step 500 for continued monitoring for a trigger event.

In Step 504, content for presentation to the user is selected from a multitude of contents that are available. The identification of the content may be performed by a content selection engine, such as the content selection engine (150) executing the content selection logic (152).

In one or more embodiments, a set of rules is used to identify the content for presentation to the user. The set of rules may have been established to provide a selection of content that is suitable, in view of the system-internal context and/or system-external context. The most suitable content may be the content that is most beneficial or most needed by the user to enable the user to respond to a current situation (e.g., an error). By providing the most suitable content to the user, various metrics such as risk, time required to obtain a solution, cost, effort, etc. may be minimized. As a result, the content that is likely to be most appropriate based on the urgency, risk, and/or required expertise may be selected. Numerous examples for the content selection in Step 504 are provided below.

The following criteria may be used to design rules for a selection of content. The criteria may be applicable to a telepresence scenario in which a remote user and/or a local user are potential targets for receiving content. The following examples may be applicable to the robotic surgical system introduced in FIG. 2A, FIG. 2B, and FIG. 3. Various criteria that may be used to establish rules are subsequently provided. Examples for rules, based on these and other criteria are provided below. While rules that are based on the following criteria may be specific to certain computer-assisted medical systems, other rules based on the same or other criteria may be established for other computer-assisted medical systems, without departing from the disclosure.

(i) Type of telepresence event: Methods and systems as described may support different types of telepresence events, such as remote proctoring, remote mentoring, remote case observation, remote technical support, etc. Depending on the type of telepresence event, a remote user may benefit from different types of content.

(ii) Local user (or team of local users) with whom the remote user is interacting, using the telepresence: Content relevant to the remote user may depend on who the local user is, with whom the remote user is communicating. For example, a local user may be a bedside assistant, a surgeon operating the computer-assisted medical system, a circulating nurse outside the sterile field, etc. Different types of local user may perform different tasks and may have different roles. The content selection may, thus, consider the type of local user and/or the current task of the local user.

(iii) Location of the local user with whom the remote user is interacting, using the telepresence: It may matter where the local user is located in the operating room. For example, the local user may be inside or outside a sterile field, may have a certain distance to components of the computer-assisted medical system, may be facing the computer-assisted medical system in different ways (behind of or in front of the computer-assisted medical system), etc.

(iv) State of computer-assisted medical system: Content relevant to the remote user may depend on the state of the computer-assisted medical system (including whether the computer-assisted medical system is powered on, the components of the computer-assisted medical system that are connected, whether the operator (surgeon) is in control of the computer-assisted medical system, etc.) The state of the computer-assisted medical system may also include error conditions such as an error of a manipulator arm, including which manipulator arm is involved in the error and the type of error (such as a collision between manipulator arms, between a manipulator arm and the patient, etc.), instrument failure, instrument engagement failure, etc.

(v) Current phase of an ongoing procedure: Content relevant to the remote user may depend on the phase of an ongoing procedure, e.g., whether the patient is docked, the surgery is in-progress, suturing is performed after the surgery, the surgery is completed, etc.

(vi) User preferences: Content relevant to the remote user may also depend on the remote user's preference.

A selection of example rules is subsequently provided.

(i) Manipulator arm collision (outside patient): A rule indicates that upon detection of the collision, the content to be provided is a view of the collision. The exact type of the view of the collision may depend on the local user being present near the site of the manipulator arm collision. Different views may be provided to different users (e.g., a remote user for technical support, a surgeon controlling the manipulator arms, the nurse in the sterile field, etc.). A detailed example is provided below in reference to FIG. 6A and FIG. 6B.

(ii) Collision of an input device (e.g., a haptic manipulandum) with other structural components at the user control system: A rule indicates that upon detection of the collision, the content to be provided is a view of the collision. The exact type of the view of the collision may depend on whether the operator of the input device (e.g., a surgeon) is engaged with the user control system. The content may be presented to a remote user, e.g., a technical support person or a proctor.

(iii) Suboptimal kinematic configuration of an input device: The input device may be poorly positioned, relative to the instrument controlled by the input device, within the available workspace. A rule indicates that upon detection of the suboptimal kinematic configuration of the input device (e.g., based on a deviation of the actual kinematic configuration from a known good kinematic configuration and/or based on poor movement of the instrument controlled by the input device in an endoscopic view), the content to be provided is a view of the kinematic configuration of the input device. The view may include the local operator while operating the input device. The content may be presented to a remote user, e.g., a technical support person or a proctor, or to a local user.

(iv) Suboptimal kinematic configuration of one or more manipulator arms: One or more of the manipulator arms may be poorly positioned, increasing the likeliness of a collision or other suboptimalities such as kinematic singularities. A rule indicates that upon detection of the suboptimal kinematic configuration (e.g., based on internally tracking the kinematic configuration or image-based detection), the content to be provided is a view with an alert indicating that the manipulator arms are suboptimally positioned (e.g., too close after an instrument change). The content may be provided to a remote user e.g., a technical support person, or a proctor or to a local user such as the surgeon operating the manipulator arms, or a bedside nurse in proximity to the manipulator arms.

The prior examples are based on a content selection using one or more rules. Other methods for content selection may be used, without departing from the disclosure. For example, rules may be implicitly encoded by a learning model. The learning model may have been trained and may be updated based on previous content selections by users. More generally speaking, the training may be driven by observations of how users have solved problems and/or what type of assistance (e.g., in the form of content) they received. For example, the training may be based on monitoring ongoing or past telepresence sessions for content that is/was presented or requested, the interaction of users with the content (e.g., when a user highlights a particular aspect of content or zooms into content), etc. The training may further be based on monitoring teaching sessions, when an experienced user teaches an inexperienced user, based on how procedures are commonly performed.

In Step 506, the presentation format for presenting the content to the user may be selected. The selection of the presentation format may be performed based on satisfying certain criteria as subsequently discussed.

The selection of the presentation format may involve selecting a display for presenting the content. The selection of the display may depend on the user who is supposed to receive the content. For example, some local and/or remote proctors, different types of support persons, etc., may receive the content through an augmented reality display, a virtual reality display, a head mounted display, a monoscopic or stereoscopic display screens integrated in the medical device, a tablet, one or more monitors, etc. Other users, e.g., nurses in the operating room, may receive the content through stationary displays.

The selection of the presentation format may further involve selecting from alternative possible visualizations when the content may be visualized in different ways. For example, certain features may be visible in a point cloud view, in a mesh view, in a system model view. Additional views may include an endoscopic view and a user control system view. The selection of the presentation format may involve selecting the visualization in which a feature of interest is particularly visible. Consider, for example, a collision of two manipulator arms. The collision may be visible in the point cloud view, in the mesh view, and in the system model view. However, the collision may be difficult to see in the point cloud view and in the mesh view. In contrast, the collision may be easily visible in the system model view. Accordingly, the system model view may be selected over the point cloud view and the mesh view. Further, the system model view may allow any level of zooming, panning, 3D orienting, etc., thereby further increasing an assessment of the collision by the user. In one embodiment, the selection of the presentation format manipulates the selected content by zooming, panning, and/or orienting operations to improve the visibility of the feature of interest. The operations of Step 506 may further be extended to multi-view scenarios in which multiple selections of content may be combined to form a multi-view. Multiple selections of content may be beneficial when a current scenario is complex and/or when multiple different views are available that are considered beneficial. For example, it may be instructive to show not only a system model view but also the actual image view that is related to the system model view. In case of an error to be addressed, the underlying problem may be more easily visible in the abstracted system model view, whereas addressing the error may be easier based on seeing the actual image view that directly corresponds to the actual physical world.

In one or more embodiments, predefined presentation templates are used for the presentation format. The presentation templates may be linked to particular contexts.

For example, a database that associates predefined contexts and predefined templates may be queried to identify the appropriate predefined template given the current context. The identified predefined template may then be applied to the content when presenting the content.

The template may define types of content to which the template applies, a configuration of the content (e.g., a particular view of a 3D model), an arrangement of the content in a display (e.g., a view of a 3D model next to an endoscopic view), UI elements (e.g., elements that allow the viewing user to annotate, rotate view, adjust image, take over control of robot, etc.), modifications/augmentations to the content (e.g., adding a graphical overlay to video or compositing two types of video).

In Step 508, the content for presentation may be provided to the user. The content may be provided to the user using the presentation format. The content selection engine (150) may facilitate the providing the content for presentation to the user, by sending the content to a rendering engine or any other system. Accordingly, the content for presentation may be rendered as specified by the presentation format. More specifically, Step 508 may involve obtaining the content from a local or remote data storage or from a live content source and transmitting the obtained content to a display device (in some cases over a network). Step 508 may further involve processing obtained content before presenting to the user. The processing may include rendering, transforming, compositing multiple content, augmenting, etc. Step 508 may also involve generating new content based on the selected content and storing the new content in a data storage for later access by a user.

The use case scenario described below is intended to provide an illustrative example of the method for coordinating content presentation described in the flowcharts of FIG. 4A, FIG. 4B, and FIG. 5. The use case scenario is based on a computer-assisted medical system as shown in FIG. 2A, FIG. 2B, and FIG. 3. The methods described by FIG. 4A, FIG. 4B, and FIG. 5 are not limited to the use case scenario.

Consider a scenario in which a telepresence configuration as shown in FIG. 1B is used to resolve a problem with a computer-assisted medical system. In the example, the problem is a manipulator arm collision (which may be between two manipulator arms or between a manipulator arm and another surface, e.g., the patient). A local user (e.g., a nurse within the sterile field) may be unable to resolve the manipulator arm collision and therefore contacts a remote user (e.g., a remote assistant).

Figure 6A:
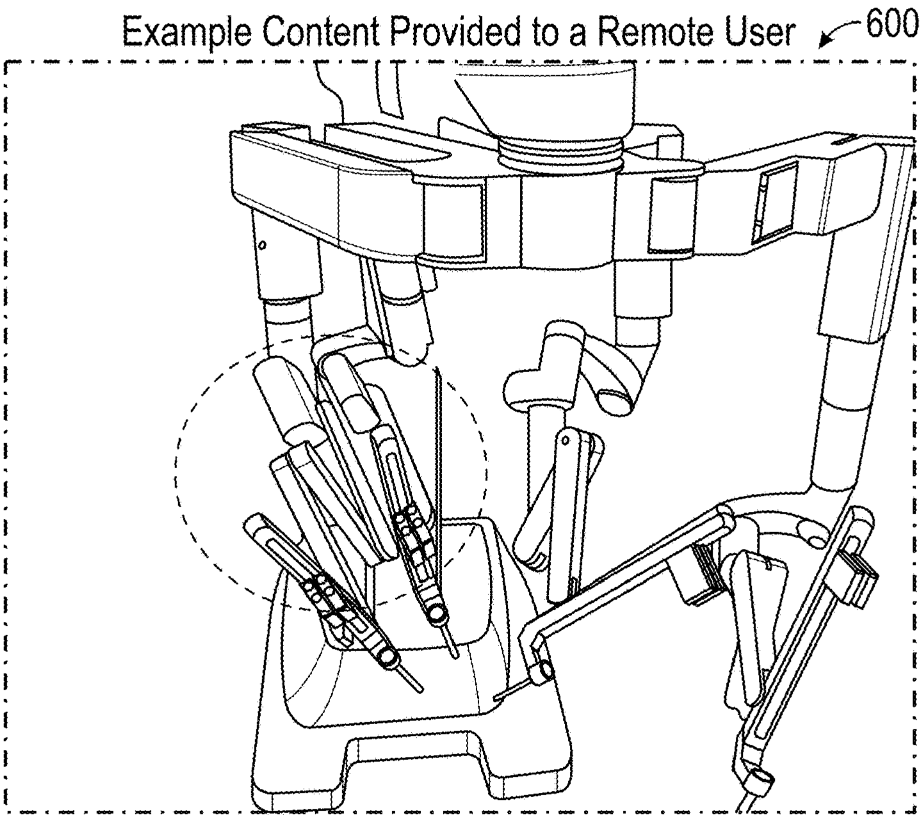
FIG. 6A and FIG. 6B show examples of content that may be provided to users, in accordance with one or more embodiments.

FIG. 6A shows example content (600) that is automatically provided to the remote user when the remote user is contacted. The content is selected based on the current context. Specifically, in the example, the system-internal context of the computer-assisted medical system indicates a manipulator arm collision. A rule indicates that the system model of the computer-assisted medical system is the appropriate content to be provided to the remote user. The system model may be the appropriate content in comparison to other alternative content, for various reasons. Compared to an image or video of the computer-assisted medical system, the system model does not include distracting background while accurately reflecting the current configuration of the computer-assisted medical system, including the kinematics. Further the system module may be freely manipulated (zoom, pan, 3D rotation), enabling the remote user to closely examine the manipulator arm collision (dashed circle in FIG. 6A). Accordingly, the remote user may be able to rapidly assess the manipulator arm collision. In the example, the view is modified to highlight (dashed circle) the collision. Alternative methods may be used to increase the visibility of the collision.

Figure 6B:
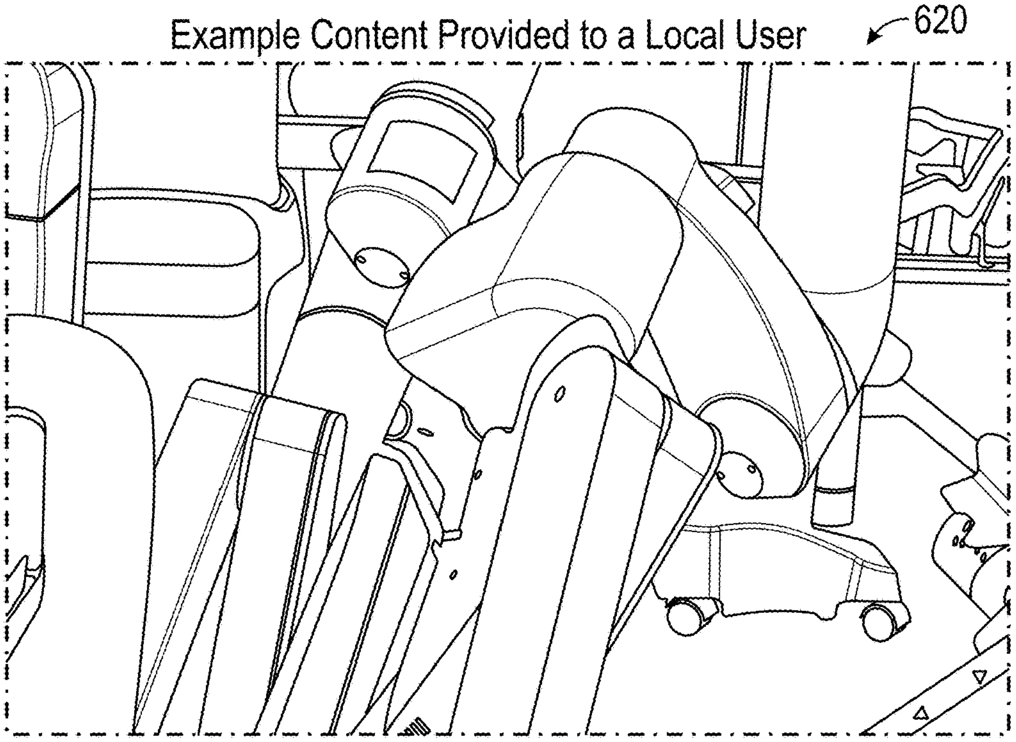

Further, to enable the local user to address the underlying issue with the assistance of the remote user, the content (620), shown in FIG. 6B is provided to the local user. The content includes an augmented reality (AR) visualization that highlights the colliding manipulator arm elements to guide the local user's attention to the colliding arm elements. The AR visualization is selected over other alternative content because it is particularly useful. Specifically, the AR visualization is selected because the context indicates that the local user wears AR glasses. An AR visualization that dynamically updates the view as the local user is moving relative to the computer-assisted medical system is superior to a static display on a screen. The highlighting in the AR visualization is directly superimposed on the actual colliding manipulator arm elements, rather than requiring a separate image of the computer-assisted medical system. Based on the content automatically provided to the remote user (FIG. 6A) and the content automatically provided to the local user (FIG. 6B), both the local and remote user have an understanding of the manipulator arm collision issue and are able to resolve the issue, based on instructions provided by the remote user to the local user.

Another example of a view that may be provided to a user is a multi-view, which may be automatically generated by the content selection engine under certain circumstances, for example, when the complexity of a current scenario makes it beneficial to provide a composite of different views. In one particular scenario, this may help a remote user follow a complex surgical procedure which may be difficult to represent in a single view. In the example, the multi-view may include multiple endoscopic views that are simultaneously available for viewing by the remote user. Multiple views may be shown side-by-side or arranged in other ways. The multi-view may contain any combination of content and may be viewed using any type of viewing device, including a console display a head-mounted display, etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A coordination system for coordinating content presentation associated with a session involving use of a computer-assisted medical system, the coordination system comprising:

a session awareness engine configured to:

obtain data from the computer-assisted medical system currently being used by a surgeon performing a medical procedure in an operating room, the data indicative of an operational state of the computer-assisted medical system; and determine a context of the session based on the data; and a content selection engine configured to:

select a first content for presentation to a remote user of the computer-assisted medical system from a plurality of contents by applying a content selection logic to the context of the session;

select a second content for presentation to a local user of the computer-assisted medical system from the plurality of contents by applying a content selection logic to the context of the session, wherein the first content and the second content are selected to enable the remote user to support, via the first and second content, the local user, wherein, to provide the support, the remote user performs a remote task entirely outside the operating room, and facilitate presentation of the first content and the second content to the remote user and the local user, respectively.

2. The coordination system of claim 1, wherein the session awareness engine comprises a system awareness engine configured to:

determine a system-internal context based on the data, and wherein the context of the session comprises the system-internal context.

3. The coordination system of claim 2, wherein the data obtained from the computer-assisted medical system is first data, wherein the system awareness engine is further configured to obtain second data from a data source different from the computer-assisted medical system, and wherein determination of the system-internal context is further based on the second data.

4. The coordination system of claim 1, wherein the data obtained from the computer-assisted medical system is first data, wherein the session awareness engine comprises an environment awareness engine configured to:

obtain second data from a data source different from the computer-assisted medical system; and determine a system-external context based on the second data, and wherein the context of the session comprises the system-external context.

5. The coordination system of claim 4, wherein determination of the system-external context is further based on the first data.

6. The coordination system of claim 4, wherein the data source is an image capture device, and wherein the second data includes image data.

7. The coordination system of claim 4, wherein the system-external context comprises at least one state selected from a group consisting of:

a type of the local or remote user;

a type of session;

a spatial location of the local user;

a preference of the local or remote user;

a type of the medical procedure associated with the session;

a phase of the medical procedure associated with the session; and information about a patient on which the medical procedure is performed.

8. The coordination system of claim 1, wherein the content selection engine is further configured to:

select a presentation format of the first content for the presentation to the remote user.

9. The coordination system of claim 8, wherein selecting the presentation format comprises at least one selected from the group consisting of zooming, panning, and 3D orienting the first content, based on the context.

10. The coordination system of claim 8, wherein selecting the presentation format comprises selecting a display for presenting the second content to the local user.

11. The coordination system of claim 1, wherein the content selection logic comprises at least one selected from the group consisting of:

a rule, and a decision-making algorithm, trained based on prior content selections.

12. The coordination system of claim 1, wherein the plurality of contents comprises at least one selected from the group consisting of:

a preoperative data view;

a point cloud view;

a mesh view;

a system model view;

an endoscopic view;

a user control system view; and a view of an operating environment external to the computer-assisted medical system.

13. The coordination system of claim 1, wherein the computer-assisted medical system comprises a robotic manipulation system, the robotic manipulation system comprising a manipulator arm configured to support an instrument on the manipulator arm.

14. The coordination system of claim 13, wherein obtaining the data from the computer-assisted medical system includes obtaining parameters from the robotic manipulation system, the parameters comprising at least one selected from the group consisting of:

a kinematic configuration of the manipulator arm;

a kinematic configuration of the instrument;

a type of the instrument supported by the manipulator arm;

an activated control mode of the robotic manipulation system;

a docking state of a cannula;

whether the robotic manipulation system is powered;

whether an operator of the robotic manipulation system is engaged with a user control system;

hardware serial numbers;

firmware versions;

installed hardware modules, installed software modules;

an error of the robotic manipulation system; and a warning of the robotic manipulation system.

15. The coordination system of claim 13, wherein the context of the session includes system-internal context indicative of a collision of the manipulator arm, and wherein the first content for presentation is a system model view showing the collision.

16. The coordination system of claim 15, wherein the system-internal context is indicative of a location of the collision, and wherein the second content for presentation is an augmented reality view highlighting the location of the collision.

17. The coordination system of claim 1, wherein the first content is selected by the content selection engine in real-time while the computer-assisted medical system is operating.

18. The coordination system of claim 1, wherein the first content is selected by the content selection engine based on time stamps generated during an earlier operation of the computer-assisted medical system.

19. The coordination system of claim 1, wherein the first content for presentation to the remote user comprises a composite of different views.

20. A method for coordinating content presentation associated with a session involving use of a computer-assisted medical system, the method comprising:

obtaining data from the computer-assisted medical system currently being used by a surgeon performing a medical procedure in an operating room, the data indicative of an operational state of the computer-assisted medical system;

determining a context of the session based on the data;

selecting a first content for presentation to a remote user of the computer-assisted medical system from a plurality of contents by applying a content selection logic to the context of the session;

selecting a second content for presentation to a local user of the computer-assisted medical system from the plurality of contents by applying a content selection logic to the context of the session, wherein the first content and the second content are selected to enable the remote user to support, via the first and second content, the local user, wherein, to provide the support, the remote user performs a remote task entirely outside the operating room, and facilitating presentation of the first content and the second content to the remote user and the local user, respectively.

21. A non-transitory computer readable medium comprising computer readable program code for coordinating content presentation associated with a session involving use of a computer-assisted medical system, comprising instructions configured to:

obtain data from the computer-assisted medical system currently being used by a surgeon performing a medical procedure in an operating room, the data indicative of an operational state of the computer-assisted medical system;

determine a context of the session based on the data;

select a first content for presentation to a remote user of the computer-assisted medical system from a plurality of contents by applying a content selection logic to the context of the session;

select a second content for presentation to a local user of the computer-assisted medical system from the plurality of contents by applying a content selection logic to the context of the session, wherein the first content and the second content are selected to enable the remote user to support, via the first and second content, the local user, wherein, to provide the support, the remote user performs a remote task entirely outside the operating room, and facilitate presentation of the first content and the second content to the remote user and the local user, respectively.

22. The coordination system of claim 1, wherein the selection of the first content and the second content is performed to enable the remote user to interactively support, via the first and second content, the local user.

* * * * *